United States Patent [19]
Parker

[11] Patent Number: 5,873,362
[45] Date of Patent: Feb. 23, 1999

[54] ENDOTRACHEAL TUBE

[75] Inventor: Jeffrey D. Parker, Cincinnati, Ohio

[73] Assignee: Parker Medical Limited Partnership, Cincinnati, Ohio

[21] Appl. No.: 819,783

[22] Filed: Mar. 18, 1997

[51] Int. Cl.⁶ ................................................. A61M 16/00
[52] U.S. Cl. .............................. 128/207.14; 128/207.15; 604/280
[58] Field of Search ......................... 128/207.14, 207.15, 128/200.26, 207.17, DIG. 26, 911; 604/280, 264, 96, 94

[56] References Cited

U.S. PATENT DOCUMENTS

| | | |
|---|---|---|
| 2,458,305 | 1/1949 | Sanders . |
| 2,862,498 | 12/1958 | Weekes ................................... 604/280 |
| 3,862,635 | 1/1975 | Harrauteneian . |
| 3,964,488 | 6/1976 | Ring et al. . |
| 4,050,466 | 9/1977 | Koerbacher . |
| 4,231,365 | 11/1980 | Scarberry ........................... 128/207.15 |
| 4,423,725 | 1/1984 | Baran et al. . |
| 5,044,369 | 9/1991 | Sahota . |
| 5,318,021 | 6/1994 | Alessi ................................. 128/207.15 |
| 5,339,805 | 8/1994 | Parker ................................. 128/200.26 |
| 5,414,075 | 5/1995 | Swan et al. . |
| 5,591,130 | 1/1997 | Denton ................................. 128/207.15 |
| 5,720,275 | 2/1998 | Patil et al. .......................... 128/200.26 |

FOREIGN PATENT DOCUMENTS 2268067  1/1994  United Kingdom ................... 604/280

OTHER PUBLICATIONS

*International Search Report*, PCT/US98/04783, mailed Jul. 24, 1988 (4 pages).
Anesthesiology (76:151–152, 1992): When the Endotracheal Tube Will Not Pass Over the Flexible Fiberoptic Bronchoscope by Tatyana Katnelson, M.D., Elizabeth A.M. Frost, M.D., Erlina Farcon, M.D.; and Paul L. Goldiner, M.D.
Anaesthesia (48:672–674, 1993): Fibreoptic Intubation—influence of tracheal tube tip design by H.E. Jones, A.C. Pearce and P. Moore.
Anesth Analg (78:746–748, 1994): Facilitation of Fiberoptic Orotracheal Intubation with a Flexible Tracheal Tube by Sorin J. Brull, M.D.; Richard Wiklund, M.D.; Cynthia Ferris, M.D.; Neil R. Connelly, M.D.; Jan Ehrenwerth, M.D.; and David G. Silverman, M.D.

*Primary Examiner*—John G. Weiss
*Assistant Examiner*—V. Srivastava
*Attorney, Agent, or Firm*—Wood, Herron & Evans, L.L.P.

[57] ABSTRACT

An endotracheal tube (10) having an incomplete posterior bevel (50) extending toward, but not completely through, the anterior wall (36) and a curved lip (54) projecting from the anterior wall (36).

30 Claims, 5 Drawing Sheets

ENDOTRACHEAL TUBE

BACKGROUND OF THE INVENTION

I. Field of the Invention

The present invention relates to endotracheal tubes for ventilation of the lungs, and more particularly, to such tubes suitable for blind guided intubation.

II. Description of Prior Art

When a patient stops breathing, it is imperative that effective ventilation be instituted as soon as possible. Ventilation is best accomplished by forcing air through an endotracheal tube inserted through the mouth and laryngeal opening and into the trachea (in which case the tube may be referred to as an orotracheal tube). The endotracheal tube is usually a preformed, semi-flexible tubular member having a gas flow lumen extending therethrough. The tube has an arcuate shape imparted to it and the distal tip is usually cut completely across at an angle to define a beveled edge to facilitate its insertion between the vocal cords.

The usual method of orotracheal intubation relies on a blade laryngoscope by which to visualize the laryngeal opening so as to facilitate insertion of the tube. The endotracheal tube used to intubate with the blade laryngoscope is usually introduced into the laryngeal opening from the right side thereof (i.e., the patient's right side). To facilitate this procedure, the distal tip is beveled on its side relative to the curvature of the tube (i.e., the tube is cut with a left side-facing bevel that extends at an angle down from the left aspect of the tube through the right aspect) such that the terminal tip defines a right-sided chisel point, which obstructs the view of the vocal cords as little as possible as it approaches those cords and provides a suitably narrow contour for insertion therebetween, and a left-sided elliptical hole circumscribed by the left side-facing beveled edge. Intubation with the blade laryngoscope presents significant difficulties and risks, however. In addition to possible injury or trauma to the patient in the utilization of the blade laryngoscope, it is not uncommon for the orotracheal tube to be accidentally inserted into anatomical spaces surrounding the larynx, such as the closely adjacent esophagus. Such misintubation, if not quickly recognized and corrected, may have fatal consequences.

Another approach to intubation is so-called blind intubation in which a guide device is inserted into the throat to guide the orotracheal tube into the laryngeal opening without requiring visualization of the laryngeal opening. I have developed blind intubation guides which both minimize injury and trauma in use, and also substantially reduce the risk of misintubation. Such intubation guides are shown, for example, in my U.S. Pat. No. 5,339,805 and my U.S. Patent Application entitled "Orotracheal Intubation Guide", filed concurrently herewith. The disclosures of my aforesaid '805 patent and concurrently-filed patent application are both incorporated herein by reference in their entireties. With some blind intubation guides such as mine, the endotracheal tube is advanced through the guide into the laryngeal opening along the midline of that opening rather than obliquely from the side of that opening, as with a blade laryngoscope. Thus, the side-facing bevel of the tube tip may be of no useful benefit and, indeed, may be disadvantageous in that the right-sided chisel point may become impacted on the right side of the larynx, and the left-facing elliptical hole may snag on left-sided laryngeal features, such as the left arytenoid and corniculate cartilages, thus preventing the tube from advancing into the trachea.

Another blind intubation technique is to railroad the tube over another member such as a tubular orotracheal introducer. In such a technique, the introducer is inserted into an orotracheal tube and extends through the tube lumen beyond the distal tip. The forward end of the introducer is inserted through the laryngeal opening into the trachea, and the tube is railroaded downward over the introducer into the trachea. Here again, the side-beveled configuration of the tube tip predisposes it to become impacted or hung-up on anatomical features of the larynx for the same reasons described above.

An endotracheal tube proposed in U.S. Pat. No. 4,050,466 has a rear-facing bevel (i.e., the tube tip is cut at an angle that extends down from the outer surface of the tube's convex posterior wall through the outer surface of the tube's concave anterior wall), rather than a side-facing bevel. The rear-facing bevel moves the chisel point of the bevel tip from a lateral aspect of the tube to the anterior aspect. I have discovered, however, that the chisel point created by this complete posterior bevel is too broad, and too anteriorly disposed. As a result, the tube may have a tendency to become impacted on the posterior base of the epiglottis or hung up on the vocal cords at the anterior commissure of the glottis where the space between the vocal cords is the narrowest. Even if the tube successfully passes through the glottis, the chisel point would tend to become lodged on or between the cartilaginous rings within the trachea thus preventing further advancement in the trachea.

SUMMARY OF THE INVENTION

The present invention provides an improved endotracheal tube, especially for use with blind intubation guides and orotracheal tube introducers, which minimizes the tendency of the tube to snag on anatomical features of and within the larynx and trachea. To this end, and in accordance with principles of the present invention, the distal tip of the endotracheal tube is provided with only a partial or incomplete posterior or rear-facing bevel which allows the tube to slide down the midline of the rear wall of the larynx without snagging the arytenoid cartilages, which are lateral thereto. The partial posterior bevel leaves a depending projection or lip of the anterior tube wall rather than a chisel point. The partial posterior bevel does not cut completely through the anterior wall of the tube, but instead stops short thereof such as at the inner surface of the anterior wall. The depending lip thus created is advantageously tapered to facilitate its insertion into the narrow opening (glottis) between the vocal cords, and is also curved posteriorly back toward the axis of the tube lumen to define a convex bearing surface which will slide easily down the inner surface of the epiglottis and the inner surface of the anterior tracheal wall without becoming impacted on the epiglottis, anterior commissure, or tracheal rings. The downwardly extending convex bearing surface of the lip may be aligned with the outer anterior tube wall or offset therefrom, and may include a fin on its inferior aspect to facilitate insertion into the glottis.

The lip is semi-flexible and confined to a small size which stops short of the midline axis of the tube distal tip so that if the lip impacts in the body and flexes upward, it will not occlude the lumen of the tube or obstruct the flow of air to the patient's lungs. Similarly, the lip will not obstruct the passage of a bronchoscope fiberbundle or suction catheter passed through and beyond the tube. Instead, the lip is flexed backward by such tubular instruments as they pass, and returns to its original shape when they are withdrawn from contact with the lip. The lip is tapered to a narrowly rounded distal edge to facilitate passage of the tube tip into and through the glottic opening. Where the lip is simply curved inwardly toward the tube lumen, the angle of the curved lip may be about 45° to 55° measured from a line tangent to the lip relative to the midline axis, and is advantageously at an angle of about 50°. Where the lip includes a portion offset outwardly of the tube and then curves back toward the midline axis, the lip curves at an angle of about 30° to 40°. If additional ventilating capacity is desired, one or two holes, known as "Murphy eyes", may be provided, for example, through opposed sides of the tube wall adjacent the distal tip above and lateral to the posterior bevel.

By virtue of the foregoing, there is thus provided an endotracheal tube which can be passed through the mouth into the larynx and trachea without becoming impacted or snagged on anatomical features of and within the larynx and trachea, such as the cartilages in the rear wall of the larynx, the vocal cords, vocal folds, epiglottis, and anterior tracheal rings. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figures 1, 2, 3, 6:
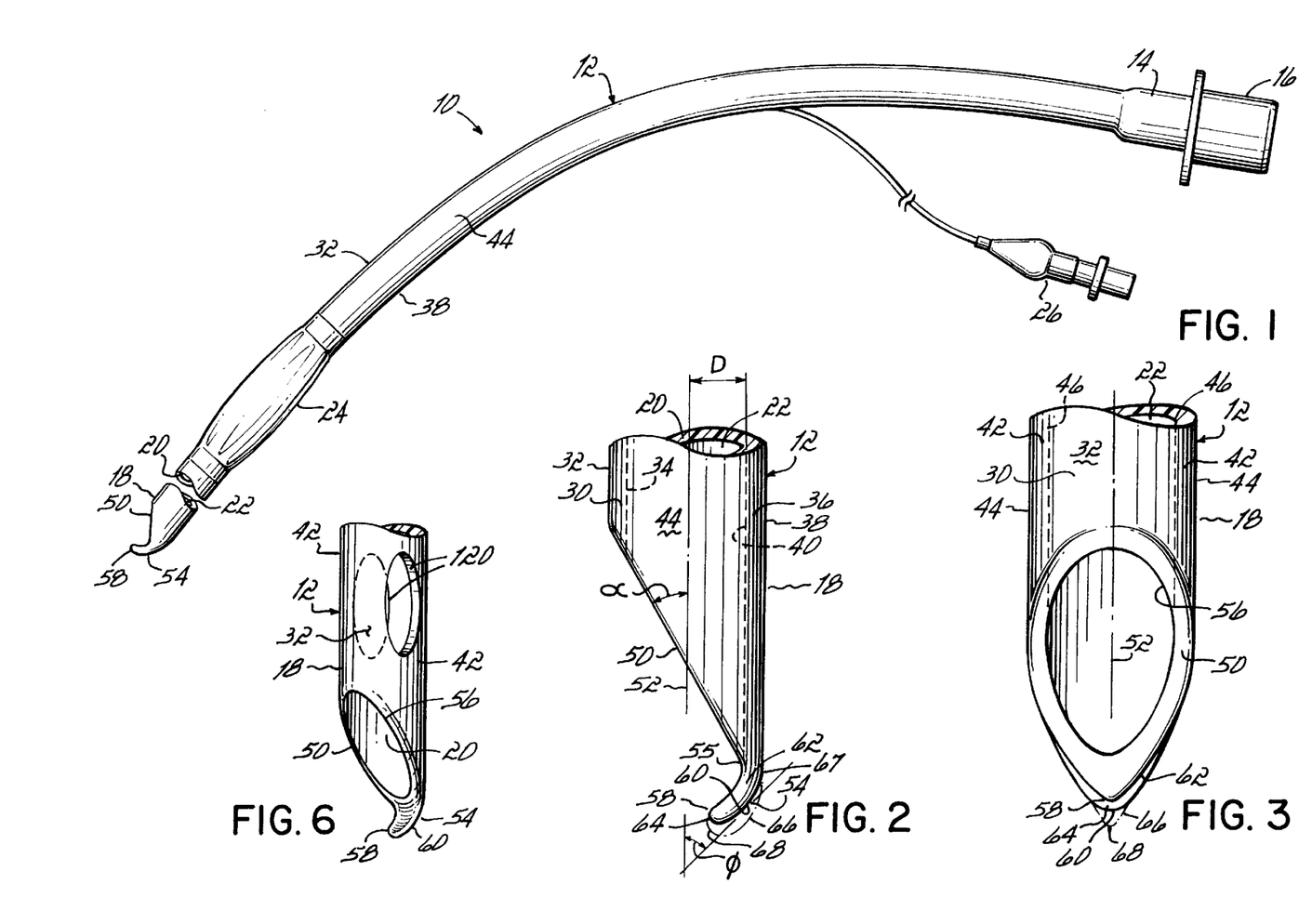
FIG. 1 is a left side elevational, partially broken away, view of a first embodiment of an endotracheal tube in accordance with the principles of the present invention.
FIG. 2 is a close-up, left side elevational view of the distal end of the tube of FIG. 1.
FIG. 3 is a close-up, front elevational view of the distal end of the tube of FIG. 1.
FIG. 6 is close-up, left side elevation view of the distal end of an alternative embodiment of an endotracheal tube in accordance with the principles of the present invention.
Figure 4A:
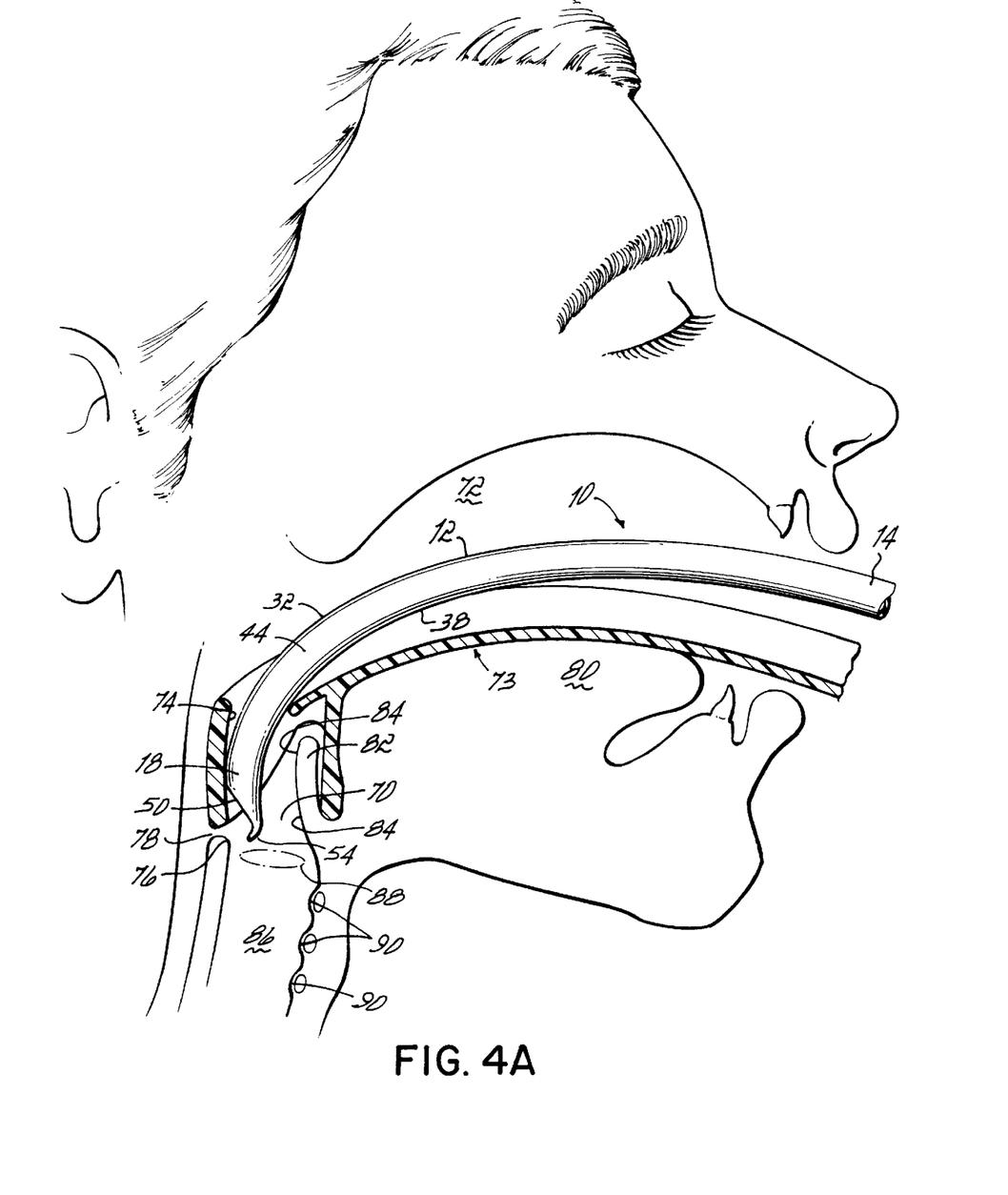
FIGS. 4A and 4B are schematic illustrations, partially cut-away, showing the tube of FIG. 1 in use with a blind intubation guide for purposes of explaining the principles of the present invention.
Figure 4B:
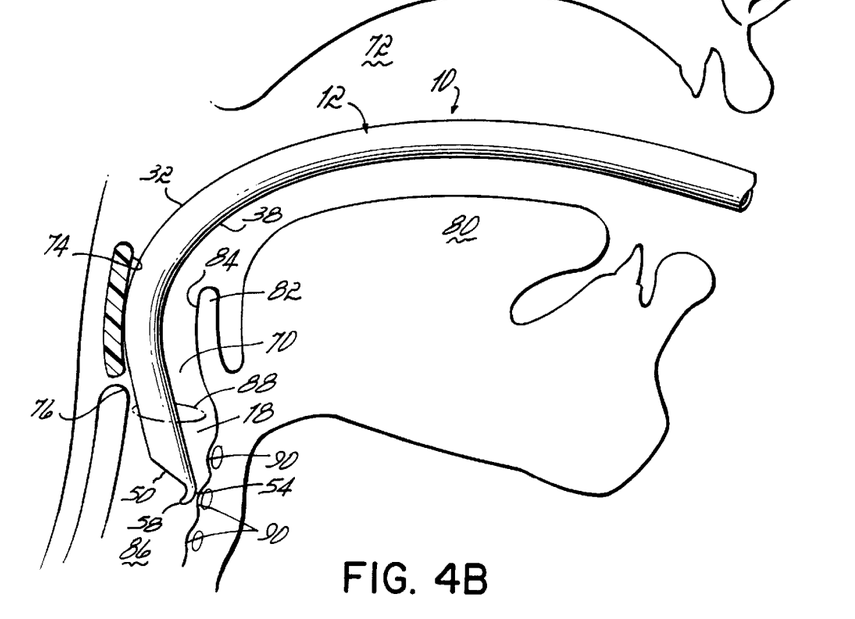

With reference to FIGS. 1–3, there is shown an endotracheal tube 10 constructed in accordance with the principles of the present invention. Tube 10 is defined by an elongated plastic tubular member 12 (such as of polyvinyl chloride or plasticized polyvinyl chloride) having a proximal end 14 to which is removably attached a connector piece 16, and a distal tip end 18. The wall 20 of member 12 defines therein a gas flow lumen 22 opening into the proximal end 14 and distal end 18 for flow of gas, such as oxygen, to ventilate a patient. An inflatable cuff or balloon 24 is provided adjacent distal end 18 and coupled to an inflation port 26 as is typical for standard, adult endotracheal tubes. For smaller size tubes, cuff 24 and port 26 may be eliminated.

Tubular member 12 has a generally arcuate shape as seen in FIG. 1. With specific reference to distal tip 18, tube 12 has a posterior wall aspect 30 with outer surface 32 and inner surface 34, an anterior wall aspect 36 with outer surface 38 and inner surface 40, and lateral wall aspects 42 each with an outer surface 44 and an inner surface 46 extending between posterior and anterior wall aspects 30 and 36. The inner surfaces 34, 40, and 46 cooperate to define gas flow lumen 22.

In accordance with the principles of the present invention, tip end 18 is provided with a partial or incomplete posterior (i.e., rear-facing) bevel 50 extending at an angle α of about 30° (measured relative to the midline axis 52 of distal tube end 18) from posterior outer surface 32 toward anterior wall aspect 36, but not completely through wall aspect 36 so as to leave a depending projection or lip 54 of anterior tube wall material 36. Advantageously, bevel 50 terminates at inner anterior wall surface 40 as at 55. Posterior bevel 50 defines an elliptically-shaped opening 56 (FIG. 3), the major diameter of which intersects midline axis 52 and lip 54. Lip 54 is sized such that its extent from end 55 of bevel 50 to lip free edge 58 is less than the distance D between the axis 52 and the inner anterior wall surface 40 so as to stop short of midline axis 52 and not occlude opening 56 should lip 54 be flexed upward toward that opening. A curvature is advantageously imparted to lip 54 such that lip 54 curves back along a line intersecting the major diameter of opening 56 toward axis 52. Lip 54 projects at an angle ø measured between a line tangent to the midpoint of inferior or outer surface 60 of lip 54 and midline axis 52 of between about 45° and 55°, and advantageously about 50°. Lip 54 has lateral side edges 62 that taper and converge smoothly into free edge 58 which is provided with a rounded bottom 64. A fin 66 (shown in dotted line in FIGS. 2 and 3) may be included on outer surface 60 running along the midline axis of lip 54. Fin 66 constitutes a tapered extension of surface 60 and progressively narrows from its origin 67 (confronting bevel end 55) to its free end 68 adjacent lip free edge 58. Lip 54 is semi-flexible so as to yield and flex on impact. By way of example, lip 54 may be flexed backward away from bevel 50 by instruments (not shown) passed through tube 10 and beyond bevel 50, but will return to its original position when such instruments are withdrawn from contact with lip 54.

The incomplete bevel 50 and lip 54 of endotracheal tube 10 make it particularly suitable for those situations in which the tube is to enter the laryngeal opening 70 of a human or animal throat 72 from above as will now be described with reference to FIGS. 4A–5C. To this end, when intubation of a patient is desired to be accomplished with a blind intubation guide 73 (such as that shown in my aforementioned '805 and/or concurrently-filed patent application), a guide wall 74 (shown schematically in FIGS. 4A and 4B) is caused to be positioned relative to the posterior edge 76 of the laryngeal opening 70 so as to be, in effect, contiguous therewith (i.e., such that any gap 78 thereat is not sizable enough for the tip end 18 of tube 10 to pass therethrough). The guide wall 74 thus defines a bearing surface along which an endotracheal tube may be directed into the laryngeal opening 70. To this end, the posterior bevel 50 may be seen as facing, and thus sliding along, guide wall 74 as tube 10 passes towards laryngeal opening 70 as shown schematically in FIG. 4A (note that cuff 24 has been eliminated for sake of simplicity). As may also be envisioned from FIG. 4A, the curvature of lip 54 causes outer surface 60 and/or fin 66 thereof to serve as a bearing surface to slide along aspects of the guide device that pass over the tongue 80 and epiglottis 82.

The central position of lip 54 further serves to facilitate the trajectory of tip end 18 into and through laryngeal opening 70. In this regard, and as will be appreciated from FIGS. 4A and 4B, while posterior bevel 50 helps to slide tube tip 18 over the posterior edge 76 of opening 70, curved lip 54 and/or fin 66 serve to avoid snagging of tube tip 18 on the rear surface 84 of epiglottis 82, the vocal cords (as represented by glottis 88), and/or the cartilaginous rings 90 within trachea 86 (only three shown). Thus, the curvature of outer surface 60 of lip 54 and/or fin 66 provides a bearing surface than deflects the tube tip 18 in a sliding manner off from and/or along those anatomical processes such that tube tip 18 may be fully inserted into trachea 86 without snagging along the way. More specifically, the curvature of lip 54 helps orient the free edge 58 such that it is aligned with the midline of the posterior commissure of the glottis 88 (where the space between the vocal cords is greatest), and is aimed away from the anterior commissure of the glottis 88 (where the space between the vocal cords is narrowest). The fin 66 is useful to help wedge apart a narrow glottic opening.

Tube 10 is pushed against guide wall 74 such that tube tip 18 passes into and beyond laryngeal opening 70. The tube continues to be pushed therealong until seated within trachea 86 as desired. Thereafter, guide wall 74 may be removed from throat 72 while leaving tube 10 in place.

Figure 5A:
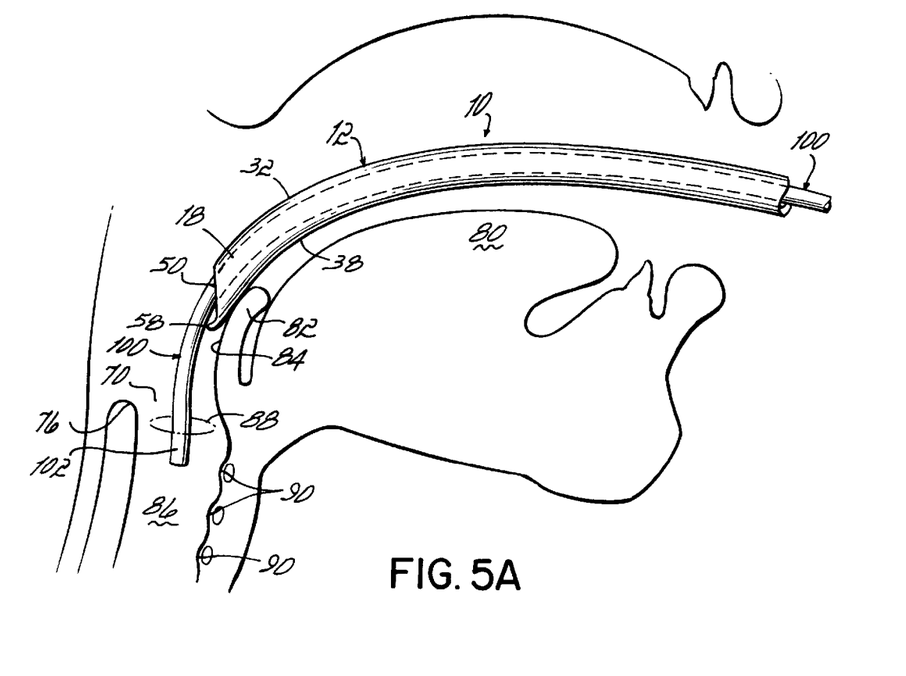
FIGS. 5A, SB, and 5C are schematic illustrations, partially cutaway, showing the tube of FIG. 1 in use with an orotracheal introducer for purposes of explaining the principles of the present invention.
Figure 5B:
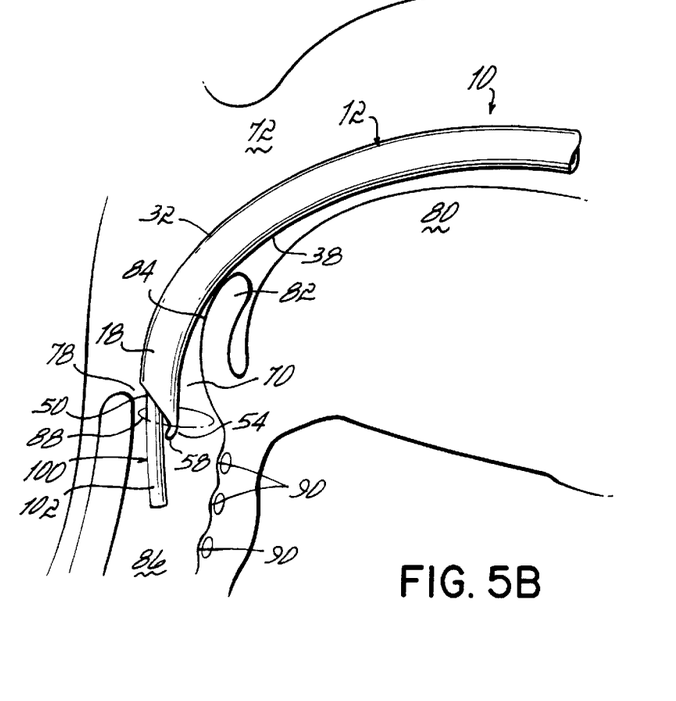
Figure 5C:
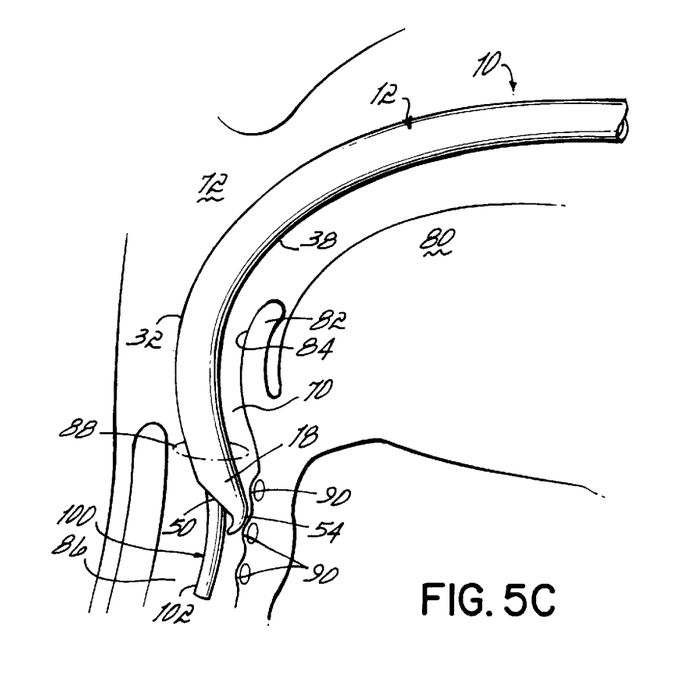

The partial bevel 50 and lip 54 of tube 10 also facilitate intubation with an orotracheal introducer (such as a tubular fiberbundle 100 of a laryngoscope) as will now be described with reference to FIGS. 5A, 5B, and 5C. To this end, introducer 100 is inserted into tube 10 from proximal end 14 thereof such that a distal portion 102 of introducer 100 projects out beyond distal tube end 18. Distal end 102 of introducer 100 is inserted into the trachea 86 and tube 10 is then railroaded over introducer 100. The curvature of lip 54 causes the free edge 58 thereof to be turned away from epiglottis 82 as tube tip 18 passes thereover to avoid snagging on epiglottis 82 and to facilitate sliding of bearing surface 60 and tube surface 38 down the rear surface 84 of epiglottis 82. As tube 10 is railroaded over introducer 100, bevel 50 will pass against posterior edge 78 of laryngeal opening 70 at which time rear-facing bevel helps tube tip 18 pass thereover and into laryngeal opening 70 without snagging on edge 76. The curved lip 54, meanwhile, provides a bearing surface 60 to help slide between the vocal cords at glottis 88 without snagging, as exemplified schematically in FIG. 5B (in which event, fin 66 is not necessary). Tube 10 is seated down in the trachea 86 by further railroading along introducer 100 such that bearing surface 60 of curved lip 54 will slide along cartilaginous rings 90 as tube tip 18 passes into the trachea (FIG. 5C). Thereafter, introducer may be removed by pulling it out from the proximal end 14 of tube 12.

In some applications, it may be helpful to provide additional ventilating capacity through distal end 18, in addition to opening 56. To this end, and with reference to FIG. 6, distal end 18 may be modified by inclusion of a hole or Murphy eye 120 formed completely through a lateral wall aspect 42 so as to be situated just above and lateral to posterior bevel 50, and below cuff 24. A pair of Murphy eyes may be positioned in confronting relationship such that the lateral disposition thereof provides alternate pathways for gas flow to the right and left mainstream bronchi (not shown) in case the opening 56 becomes occluded.

Figure 7:
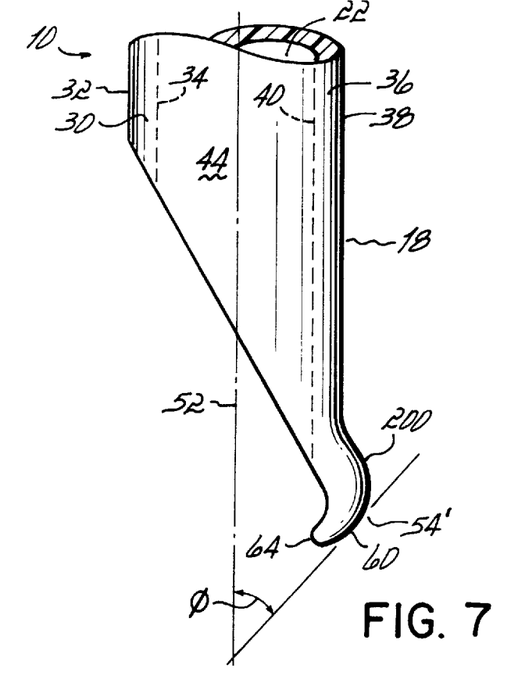
FIG. 7 is a close-up, left side elevational view of the distal end of the tube of FIG. 1 with an offset lip portion.

With reference to FIG. 7, a further alternative embodiment is shown of the distal end 18 of tube 10 in which lip 54' thereof is modified from lip 54 of the prior embodiments in that lip 54' includes a portion 200 that is offset outwardly of midline axis 52 and protrudes beyond the cylinder of outer surface 38 of anterior wall aspect 36. Lip 54' then curves back toward midline axis 52 and posterior wall aspect 30. Due to offset portion 200, however, the extent of curvature of lip 54' is such that tip 64 thereof is substantially aligned with inner surface 40 of wall aspect 36 and so does not protrude into the pathway of lumen 22. Lip 54' projects at an angle ø measured between a line tangent to the midpoint of inferior or outer surface 60 of lip 54' and midline axis 52 of between about 30° and 40°.

In use, a 7.0 mm or 7.5 mm ID endotracheal tube 10 (with or without Murphy eyes 120 and/or fin 66 as desired) is manually lubricated with a film of sterile, water-soluble, biocompatible lubricant such as Surgilube available from Altana, Inc., in Melville, N.Y. The lubricated tube 10 is inserted into the trachea 86 by use of a blind intubation guide device having a guide wall 74 as described in my aforesaid '805 patent and/or concurrently-filed patent application, after which the guide device is removed. Alternatively, a similarly-lubricated introducer 100 is inserted through tube 10 and inserted into the trachea 86 as desired. Tube 10 is then railroaded downward thereover and into the trachea 86. Introducer 100 may then be withdrawn through tube proximal end 14. In either case, the incomplete rear-facing bevel 50 and the depending lip 54 allow the tube 10 to be readily inserted into the throat 72 and trachea 86 without snagging on anatomical features of and within the laryngeal opening and trachea.

By virtue of the foregoing, there is thus provided an endotracheal tube that facilitates intubation from above the laryngeal opening, such as with a blind intubation guide and/or an orotracheal introducer, without snagging on the anatomical features of the laryngeal opening and trachea.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, lip 54 or 54' may be provided without a bevel 50 to tube end 18. Alternatively, lip 54 or 54' may not be curved and/or may not include fin 66. Further, a barium sulfate strip (not shown) may be included in wall 20 for x-ray visualization. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. An endotracheal tube comprising a tubular member extending between a proximal end and a distal end, the tubular member having first wall aspect and a second, oppositely disposed wall aspect along its length to define an airway lumen therebetween for flow of gas between the proximal end and an opening at the distal end, the tubular member having a generally pre-defined curvature, the distal end having an incomplete bevel extending from the first wall aspect toward but not completely through the second wall aspect of the tubular member to define a plane extending through the first wall aspect but not completely through the second wall aspect, the distal end further having a lip projecting beyond the plane defined by the incomplete bevel from the second wall aspect of the tubular member and curving inwardly toward the first wall aspect.

2. The endotracheal tube of claim 1 wherein the distal end has a longitudinal midline axis spaced a distance D from the second wall aspect, the lip extending to a free edge a distance less than D whereby not to occlude the opening at the distal end.

3. The endotracheal tube of claim 1 wherein the lip tapers to a free edge.

4. The endotracheal tube of claim 1 wherein the lip has an outer surface, the tube further comprising a fin extending along the lip outer surface.

5. The endotracheal tube of claim 1, the lip including a portion being offset outwardly of the second wall aspect.

6. The endotracheal tube of claim 1 wherein the incomplete bevel terminates at an inner surface of the second wall aspect.

7. The endotracheal tube of claim 1 further comprising a Murphy eye extending through the tubular member and positioned just above and lateral to the incomplete bevel.

8. The endotracheal tube of claim 1 further comprising a pair of Murphy eyes extending through the tubular member in confronting relationship and positioned just above and lateral to the incomplete bevel.

9. The endotracheal tube of claim 1 further comprising an inflation cuff associated with the tubular member.

10. The endotracheal tube of claim 1, the lip being semi-flexible.

11. An endotracheal tube comprising a tubular member extending between a proximal end and a distal end, the tubular member having a first wall aspect and a second, oppositely disposed wall aspect along its length to define an airway lumen therebetween for flow of gas between the proximal end and a single, effectively unobstructed opening at and across the distal end, the tubular member having a generally pre-defined curvature and the distal end having a lip projecting from the second wall aspect beyond the opening and curving inwardly toward the first wall aspect.

12. The endotracheal tube of claim 11 wherein the distal end has a midline axis spaced a distance D from an inner surface of the tubular member, the lip extending to a free edge a distance less than D whereby not to occlude the opening at the distal end.

13. The endotracheal tube of claim 11 wherein the lip tapers to a free edge.

14. The endotracheal tube of claim 11 wherein the lip has an outer surface, the tube further comprising a fin extending along the lip outer surface.

15. The endotracheal tube of claim 11, the lip including a portion being offset outwardly from the midline axis.

16. The endotracheal tube of claim 11 further comprising a Murphy eye extending through the tubular member and positioned just above the opening.

17. The endotracheal tube of claim 11 further comprising an inflation cuff associated with the tubular member.

18. The endotracheal tube of claim 11, the lip being semi-flexible.

19. A method of forming a generally arcuate endotracheal tube having a proximal end and a distal end with a single opening thereat, and including first and second opposite wall aspects thereof at the distal end, the method comprising:

forming an incomplete bevel across the opening at the distal end, the bevel extending from the first wall aspect to but not completely through the second wall aspect; and defining a lip projecting from the second wall aspect beyond the incomplete bevel and curving inwardly toward the first wall aspect.

20. The method of claim 19, further comprising offsetting a portion of the lip outwardly of the second wall aspect.

21. The method of claim 19 further comprising tapering the lip to a free edge.

22. The method of claim 19 further comprising defining a fin on the lip.

23. The method of claim 19 further comprising forming a Murphy eye through the tube just above the opening and lateral to the incomplete bevel.

24. The method of claim 19 further comprising forming a pair of confronting Murphy eyes through the tube just above the opening and lateral to the incomplete betel.

25. A method of forming a generally arcuate endotracheal tube having a proximal end and a distal end, the method comprising:

providing an effectively unobstructed, single opening at the distal end; and defining a lip projecting from the distal end beyond the opening and curving inwardly toward the opening.

26. The method of claim 25 wherein the distal end has a longitudinal midline axis, the method further comprising curving the lip toward the midline axis.

27. The method of claim 26 further comprising offsetting a portion of the lip outwardly from the midline axis.

28. The method of claim 25 further comprising tapering the lip to a free edge.

29. The method of claim 25 further comprising defining a fin on the lip.

30. The method of claim 25 further comprising forming a Murphy eye through the tube just above the opening.

* * * * *

UNITED STATES PATENT AND TRADEMARK OFFICE
CERTIFICATE OF CORRECTION

PATENT NO. : 5,873,362

DATED : February 23, 1999

INVENTOR(S) : Jeffrey D. Parker

It is certified that error appears in the above-identified patent and that said Letters Patent is hereby corrected as shown below:

Column 3, line 43, please replace "is close-up" with --is a close-up--;

Column 5, line 6, please replace "than" with --that--; and

Column 8, line 26 (claim 24, line 3), please correct "betel" to read --bevel--.

Signed and Sealed this

Twenty-seventh Day of July, 1999

Attest:

Q. TODD DICKINSON

*Attesting Officer*  *Acting Commissioner of Patents and Trademarks*